Nov. 8, 1949. J. S. ARMSTRONG Plant Pat. 891
CAMELLIA PLANT
Filed Oct. 9, 1947
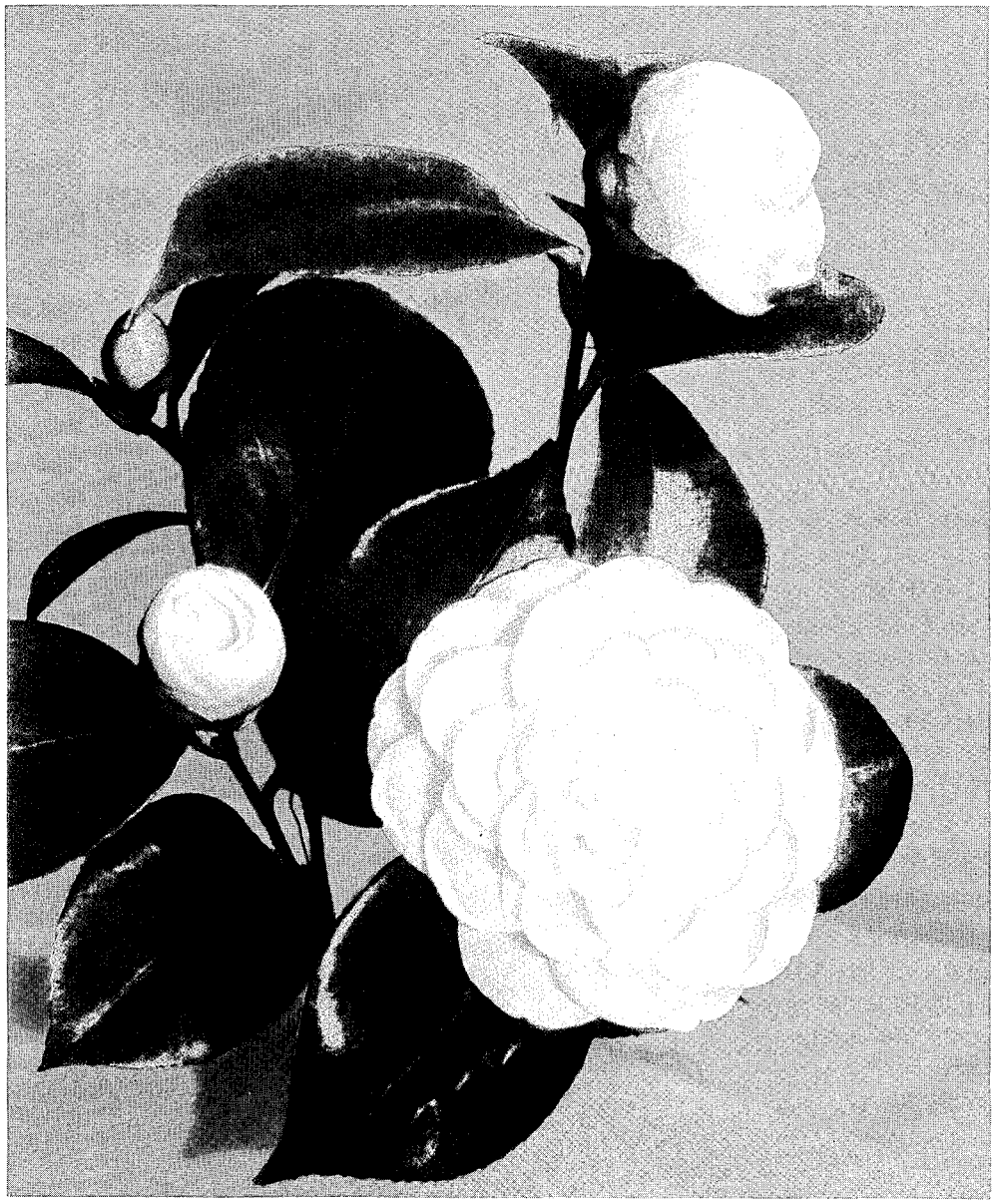
Inventor
J. S. Armstrong
By Robb & Robb
Attorneys Patented Nov. 8, 1949

Plant Pat. 891

UNITED STATES PATENT OFFICE

891

CAMELLIA PLANT

John S. Armstrong, Ontario, Calif., assignor to Armstrong Nurseries, Inc., Ontario, Calif., a corporation of California Application October 9, 1947, Serial No. 778,854

1 Claim. (Cl. 47—60)

The present discovery relates to a new and distinct variety of camellia plant, resulting from the planting of mixed lots of seeds from selected parents, and from the many seedlings, selecting and developing the variety having the desired characteristics, as hereinafter described.

As a result of the procedure above referred to, I obtain a camellia having the following combination of distinctive characteristics:

(1) A plant combining more vigor than other white flowered camellia varieties now known to commerce and a strong tendency to precociousness which is not only outstanding in its color class but among camellias of any color.

(2) The foliage which combines size and abundance not found in other varieties of camellias to the best of my knowledge.

(3) A flowering season when good white flowered camellias suitable for corsage use are scarce.

(4) A shape (involving quantity and arrangement of petals) not only distinct from other varieties of white camellias in its season, but to the best of my knowledge distinct from other varieties of white camellias in any season.

(5) White flowers with heavy substance equalling or surpassing any of the other white flowered varieties now known to commerce.

Asexual reproduction shows that the characteristics hold true through succeeding propagations.

In the drawing are shown specimens of the foliage and flowers at their different stages of development.

The following is a detailed description of the new variety, all color terminology being in accordance with Ridgway's Color Standards and Nomenclature:

Type: Half-hardy, outdoor evergreen shrub for cut flowers and garden decoration.

Class: Seedling variety of *Camellia japonica*.

Seedling: A selection from a mixed lot of seedlings obtained by harvesting and growing seed from selected seed parents.

Propagation: Holds its distinguishing characteristics through succeeding propagations by cuttings and grafting.

*Flower*

Locality where grown: Ontario, California.

Flowers borne: Single, sometimes two, axillary or terminal.

Quantity of bloom: Free, outdoors.

Continuity: One season, usually from January to March.

Fragrance: None.

Bud: Sessile.

*Before calyx breaks.—Size*—medium to large.

*Form.*—Long, pointed; with fine tomentum on the surface of the bud.

*Sepals.*—Imbricated, very broadly ovate in outline but strongly cupped about bud. Lower sepals almost scale-like, upper sepals becoming scarious when flower fully opens.

*Color.*—At base, Biscay Green, Plate XVII, shading to Apple Green, Plate XVII, and becoming Light Dull Green-Yellow, Plate XVII, at apex. Lower sepals occasionally with a very narrow margin of Snuff Brown, Plate XXIX, at upper edge.

*As first petal opens.—Size*—medium to large. *Form*—long, flat at apex. *Color*—outside and inside—white.

*Opening.*—Opens up well.

Bloom: Size, when fully open—large, 3 to 3½ inches (8 to 9 cm. in diameter).

*Petalage.*—Very double, 40 to 45 petals arranged regularly with 25 to 30 petaloids at center forming an irregular tuft with a few petaloids interspersed among petals near center.

*Form.*—Complete double, incomplete imbricated; slightly cupped, full, high center at first; petals remaining at first very loosely cupped inward; outer petals becoming later, at maturity, very loosely rolled outward.

Petals: Moderately thick; with inside and outside satiny.

*Shape.*—Outside: ovate with one notch, having an acute point. Intermediate: ovate, occasionally an acute point with one or two notches on margin of petal, apex with an acute point. Inside: ovate, lanceolate, sometimes with one notch on margin, apex with an acute point.

*Color.*—Colors may be modified by being bordered, margined, shaded with other colors.

This description of a newly opened flower was made from a camellia grown outdoors in the month of February, at Ontario, California:

*Color.*—Petals—outside surface: White, becoming Cream Color, Plate XVI, at base of petal; inside surface: White, becoming Cream Color, Plate XVI, at base of petal.

*General color effect.*—White.

*Behavior.*—Persist on plant until flowers become old, at which time flowers drop off cleanly.

*Flower longevity.*—On plant in garden—9 to 10 days in February. Cut camellias grown outdoors kept at living-room temperatures—5 days in February.

*Reproductive organs*

Stamens: Usually none, transformed into petaloids.

Pistils: Occasionally present but if present are rudimentary and distorted.

Seeds: Not known to set seeds due to poor development of pistil when present.

*Plant*

Foliage: Leaves, alternate, simple, moderately abundant, medium to large, leathery, glossy above, semi-glossy beneath.

*Shape.*—Ovate-lanceolate, with apex acuminate; base obtuse to acute; margin simply serrate.

*Size.*—5 to 7 cm. wide and 7 to 11 cm. long.

*Midrib.*—Prominent, raised on upper and under surface of leaf.

*Veins.*—Pinnate, raised slightly on upper and under surface of leaf but not prominent.

*Petiole.*—Heavy, medium-length, 8 to 10 mm. long.

*Color.*—*Mature*—upper surface—near Yew Green, Plate XXXI; under surface—near Light Cress Green, Plate XXXI. *Young*—upper surface—near Forest Green Plate XVII; under surface—near Biscay Green, Plate XVII.

Growth:

*Habit.*—Bushy; upright; much branched.

*Growth.*—Moderately heavy; vigorous.

*Main stems.*—*Color*—between Buffy Brown, Plate XL, and Olive Brown, Plate XL, becoming scurfy when several years old.

*Branches.*—*Color*—near Chestnut, Plate II.

*New shoots.*—near Spinach Green, Plate V.

I claim:

A new and distinct variety of camellia plant, substantially as shown and described and characterized as to novelty by its vigorous growing habit and strong tendency to precociousness; by the size and abundance of its foliage; and the size and color of the flowers of heavy substance, said plant also having an unusual blooming season in comparison with other known white camellias of this form.

JOHN S. ARMSTRONG.

No references cited.